United States Patent
Opie et al.

(10) Patent No.: US 9,795,712 B2
(45) Date of Patent: *Oct. 24, 2017

(54) MEDICAL IMPLANTS

(75) Inventors: David Opie, Annapolis, MD (US);
Tranquoc Thebao Nguyen, Anaheim, CA (US); Atakan Peker, Aliso Viejo, CA (US)

(73) Assignee: Crucible Intellectual Property, LLC, Rancho Santa Margarita, CA (US)

( * ) Notice: Subject to any disclaimer, the term of this patent is extended or adjusted under 35 U.S.C. 154(b) by 1467 days.

This patent is subject to a terminal disclaimer.

(21) Appl. No.: 10/524,954

(22) PCT Filed: Aug. 19, 2003

(86) PCT No.: PCT/US03/26060
§ 371 (c)(1),
(2), (4) Date: Jan. 30, 2006

(87) PCT Pub. No.: WO2004/016197
PCT Pub. Date: Feb. 26, 2004

(65) Prior Publication Data
US 2006/0149391 A1 Jul. 6, 2006

Related U.S. Application Data

(60) Provisional application No. 60/404,509, filed on Aug. 19, 2002.

(51) Int. Cl.
*A61F 2/06* (2013.01)
*C22C 45/10* (2006.01)
(Continued)

(52) U.S. Cl.
CPC ............ *A61L 27/306* (2013.01); *A61L 27/04* (2013.01); *A61L 27/50* (2013.01); *A61L 27/56* (2013.01);
(Continued)

(58) Field of Classification Search
CPC .. A61F 2310/00023; A61F 2310/00011; A61F 2310/00017; A61F 2310/00047;
(Continued)

(56) References Cited

U.S. PATENT DOCUMENTS 2,190,611 A   2/1940  Sembdner
3,989,517 A   11/1976 Tanner et al.
(Continued)

FOREIGN PATENT DOCUMENTS

EP   1063312 A1   12/2000
GB   2236325 A    4/1991
(Continued)

OTHER PUBLICATIONS

Li, et al., "Glass transition temperature of bulk metallic glasses: A linear connection with the mixing enthalpy," Journal of Applied Physics 101, 103540 (2007).
(Continued)

*Primary Examiner* — Ann Schillinger
(74) *Attorney, Agent, or Firm* — Brownstein Hyatt Farber Schreck, LLP

(57) ABSTRACT

The current invention is directed to a medical implant made of bulk-solidifying amorphous alloys and methods of making such medical implants, wherein the medical implants are biologically, mechanically, and morphologically compatible with the surrounding implanted region of the body.

24 Claims, 4 Drawing Sheets

(51) Int. Cl.
*A61L 27/30* (2006.01)
*A61L 27/04* (2006.01)
*A61L 27/50* (2006.01)
*A61L 27/56* (2006.01)
*B22D 17/00* (2006.01)
*B22D 18/04* (2006.01)
*B22D 18/06* (2006.01)
*B22D 25/00* (2006.01)
*B22D 31/00* (2006.01)
*A61B 17/72* (2006.01)
*A61B 17/80* (2006.01)
*A61B 17/86* (2006.01)
*A61B 17/00* (2006.01)
*A61F 2/30* (2006.01)
*A61F 2/32* (2006.01)

(52) U.S. Cl.
CPC ............ *B22D 17/00* (2013.01); *B22D 18/04* (2013.01); *B22D 18/06* (2013.01); *B22D 25/00* (2013.01); *B22D 31/002* (2013.01); *C22C 45/10* (2013.01); *A61B 17/72* (2013.01); *A61B 17/80* (2013.01); *A61B 17/866* (2013.01); *A61B 2017/0084* (2013.01); *A61B 2017/00858* (2013.01); *A61F 2/3094* (2013.01); *A61F 2/30767* (2013.01); *A61F 2/30771* (2013.01); *A61F 2/32* (2013.01); *A61F 2002/30535* (2013.01); *A61F 2002/30957* (2013.01); *A61F 2250/0058* (2013.01); *A61F 2310/00089* (2013.01); *A61F 2310/00952* (2013.01)

(58) Field of Classification Search
CPC .............. A61F 2/28; A61F 2002/30014; A61F 2002/30016; A61F 2250/0018; A61F 2310/00029; A61F 2310/00053; A61F 2310/00071; A61F 2310/00179; A61F 2002/30004
USPC ............................................ 623/23.72–23.76
See application file for complete search history.

(56) References Cited

U.S. PATENT DOCUMENTS

| | | | |
|---|---|---|---|
| 4,050,931 A | 9/1977 | Tanner et al. | |
| 4,064,757 A | 12/1977 | Hasegawa | |
| 4,067,732 A | 1/1978 | Ray | |
| 4,113,478 A | 9/1978 | Tanner et al. | |
| 4,115,682 A | 9/1978 | Kavesh et al. | |
| 4,116,682 A | 9/1978 | Polk et al. | |
| 4,116,687 A | 9/1978 | Hasegawa | |
| 4,126,449 A | 11/1978 | Tanner et al. | |
| 4,135,924 A | 1/1979 | Tanner et al. | |
| 4,148,669 A | 4/1979 | Tanner et al. | |
| 4,278,630 A * | 7/1981 | Scheicher | 264/122 |
| 4,289,009 A | 9/1981 | Festag et al. | |
| 4,371,912 A | 2/1983 | Guzik | |
| 4,472,955 A | 9/1984 | Nakamura et al. | |
| 4,621,031 A | 11/1986 | Scruggs | |
| 4,623,387 A | 11/1986 | Masumoto et al. | |
| 4,648,609 A | 3/1987 | Deike | |
| 4,710,235 A | 12/1987 | Scruggs | |
| 4,721,154 A | 1/1988 | Christ et al. | |
| 4,743,513 A | 5/1988 | Scruggs | |
| 4,854,370 A | 8/1989 | Nakamura | |
| 4,976,417 A | 12/1990 | Smith | |
| 4,987,033 A | 1/1991 | Abkowitz et al. | |
| 4,990,198 A | 2/1991 | Masumoto et al. | |
| 5,032,196 A | 7/1991 | Masumoto et al. | |
| 5,049,074 A | 9/1991 | Otani et al. | |
| 5,053,084 A | 10/1991 | Masumoto et al. | |
| 5,053,085 A | 10/1991 | Masumoto et al. | |
| 5,074,935 A | 12/1991 | Masumoto et al. | |
| 5,117,894 A | 6/1992 | Katahira | |
| 5,131,279 A | 7/1992 | Lang et al. | |
| 5,169,282 A | 12/1992 | Ueda et al. | |
| 5,213,148 A | 5/1993 | Masumoto et al. | |
| 5,225,004 A | 7/1993 | O'Handley et al. | |
| 5,250,124 A | 10/1993 | Yamaguchi et al. | |
| 5,279,349 A | 1/1994 | Horimura | |
| 5,288,344 A | 2/1994 | Peker et al. | |
| 5,296,059 A | 3/1994 | Masumoto et al. | |
| 5,306,463 A | 4/1994 | Horimura | |
| 5,312,495 A | 5/1994 | Masumoto et al. | |
| 5,324,368 A | 6/1994 | Masumoto et al. | |
| 5,368,659 A | 11/1994 | Peker et al. | |
| 5,380,375 A | 1/1995 | Hashimoto et al. | |
| 5,384,203 A | 1/1995 | Apfel | |
| 5,390,724 A | 2/1995 | Yamauchi et al. | |
| 5,449,425 A | 9/1995 | Renard et al. | |
| 5,482,580 A | 1/1996 | Scruggs et al. | |
| 5,567,251 A | 10/1996 | Peker et al. | |
| 5,589,012 A | 12/1996 | Hobby et al. | |
| 5,618,359 A | 4/1997 | Lin | |
| 5,711,363 A | 1/1998 | Scruggs et al. | |
| 5,735,975 A | 4/1998 | Lin | |
| 5,797,443 A * | 8/1998 | Lin et al. | 164/4.1 |
| 5,886,254 A | 3/1999 | Chi | |
| 5,950,704 A | 9/1999 | Johnson et al. | |
| 6,021,840 A | 2/2000 | Colvin | |
| 6,027,586 A | 2/2000 | Masumoto et al. | |
| 6,042,780 A * | 3/2000 | Huang | 419/36 |
| 6,044,893 A | 4/2000 | Taniguchi et al. | |
| 6,066,176 A * | 5/2000 | Oshida | 623/23.62 |
| 6,159,010 A * | 12/2000 | Rogers et al. | 433/172 |
| 6,200,450 B1 | 3/2001 | Hui | |
| 6,200,685 B1 | 3/2001 | Davidson | |
| 6,258,183 B1 | 7/2001 | Onuki et al. | |
| 6,306,228 B1 | 10/2001 | Inoue et al. | |
| 6,325,868 B1 | 12/2001 | Kim et al. | |
| 6,371,195 B1 | 4/2002 | Onuki et al. | |
| 6,376,091 B1 | 4/2002 | Croopnick | |
| 6,408,734 B1 | 6/2002 | Cohen | |
| 6,446,558 B1 | 9/2002 | Peker et al. | |
| 6,447,550 B1 | 9/2002 | Hunter et al. | |
| 6,585,772 B2 | 7/2003 | Hunter et al. | |
| 6,709,536 B1 * | 3/2004 | Kim et al. | 148/561 |
| 6,771,490 B2 | 8/2004 | Peker et al. | |
| 7,473,278 B2 | 1/2009 | Hunter et al. | |
| 7,560,001 B2 | 7/2009 | Peker | |
| 7,582,117 B2 | 9/2009 | Hunter et al. | |
| 7,896,926 B2 | 3/2011 | Hunter et al. | |
| 7,968,209 B2 | 6/2011 | Pawar et al. | |
| 8,556,987 B2 | 10/2013 | Hunter et al. | |
| 2001/0052406 A1 | 12/2001 | Kubota et al. | |
| 2002/0036034 A1 | 3/2002 | Xing et al. | |
| 2002/0050310 A1 | 5/2002 | Kundig et al. | |
| 2002/0162605 A1 * | 11/2002 | Horton et al. | 148/304 |
| 2003/0222122 A1 * | 12/2003 | Johnson et al. | 228/101 |
| 2004/0211222 A1 | 10/2004 | Hosoe | |
| 2012/0152412 A1 | 6/2012 | Opie et al. | |
| 2012/0158151 A1 | 6/2012 | Opie et al. | |

FOREIGN PATENT DOCUMENTS

| | | |
|---|---|---|
| JP | 61238423 A | 10/1986 |
| JP | 06-264200 | 9/1994 |
| JP | 7188877 | 7/1995 |
| JP | 2000-256811 | 9/2000 |
| JP | 2001303218 | 10/2001 |
| JP | 2002045960 | 2/2002 |
| WO | WO2003/064076 A1 | 8/2003 |
| WO | 2004/012620 | 2/2004 |
| WO | WO2004/045454 A2 | 6/2004 |

OTHER PUBLICATIONS

Yavari, et al., "Excess free volume in metallic glasses measured by X-ray diffraction," Acta Materialia 53 (2005) pp. 1611-1619.
U.S. Appl. No. 13/408,730, filed Feb. 29, 2012, Opie et al.

(56) References Cited

OTHER PUBLICATIONS

U.S. Appl. No. 13/408,824, filed Feb. 29, 2012, Opie et al.
Office Action dated Jun. 24, 2015, EP 10195524.3, 6 pages.
Supplemental European Search Report for International Application No. PCT/US03/26060; International Filing Date Aug. 19, 2003; Report completed Mar. 28, 2008; dated Apr. 8, 2008; 4 pgs.
Brochure entitled ProCAST . . . not just for castings!, UES, Inc., 1 page.
Catalog Cover Entitled, Interbike Buyer Official Show Guide, 1995, 3 pages.
Eshbach et al., "Section 12—Heat Transfer", Handbook of Engineering Fundamentals, 3d ed., 1975, pp. 1113-1119.
Hasegawa et al., "Superconducting Properties of Be—Zr Glassy Alloys Obtained by Liquid Quenching", May 9, 1977, pp. 3925-3928.
Inoue et al., "Zr—Al—Ni Amorphous Alloys with High Glass Transition Temperature and Significant Supercooled Liquid Region", Materials Transactions, JIM, 1990, vol. 31, No. 3, pp. 177-183.
Inoue, et al., "Bulky La—Al-TM (TM=Transition Metal) Amorphous Alloys with High Tensile Strength Produced by a High-Pressure Die Casting Method", Materials Transactions, 1993, JIM, vol. 34, No. 4, pp. 351 to 358.
Inoue, et al., "Mg—Cu—Y Bulk Amorphous Alloys with High Tensile Strength Produced by a High-Pressure Die Casting Method", Materials Transactions, 1992, JIM, vol. 33, No. 10, pp. 937 to 945.
Jost et al., "The Structure of Amorphous Be—Ti—Zr Alloys", Zeitschrift fur Physikalische Chemie Neue Folge, Bd. 157, 1988, pp. 11-15.
Kato et al., "Production of Bulk Amorphous $Mg_{85}Y_{10}Cu_5$ Alloy by Extrusion of Atomized Amorphous Powder", Materials Transactions, JIM, 1994, vol. 35, No. 2, pp. 125 to 129.
Kawamura et al., Full Strength Compacts by Extrusion of Glassy Metal Powder at the Supercooled Liquid State, Appl. Phys. Lett. 1995, vol. 67, No. 14, pp. 2008-2010.
Lyman et al., Metals Handbook, Forging and Casting, 8th ed., 1970, vol. 5, pp. 285-291 and 300-306.
Polk et al., "The Effect of Oxygen Additions on the Properties of Amorphous Transition Metal Alloys", Source and date unknown, pp. 220-230.
Tanner et al., "Metallic Glass Formation and Properties in Zr and Ti-Alloyed with Be—I The Binary Zr—Be and Ti—Be Systems", Acta Metallurgica, 1979, vol. 27, pp. 1727-1747.
Tanner et al., "Physical Properties of $Ti_{50}Be_{40}Zr_{10}$ Glass", Sripta Metallurgica, Jun. 22, 1977, vol. 11, pp. 783-789.
Tanner, L.E., "Physical Properties of Ti—Be—Si Glass Ribbons", Scripta Metallurgica, 1978, vol. 12, pp. 703-708.
Tanner, L.E., "The Stable and Metastable Phase Relations in the Hf—Be Alloy System", Metallurgica, vol. 28, 1980, pp. 1805-1815.
Zhang et al., "Amoprphous Zr—Al-TM (TM=Co, Ni, Cu) Alloys with Significant Supercooled Liquid Region of Over 100K", Materials Transactions, JIM., 1991, vol. 32, No. 11, pp. 1005-1010.

* cited by examiner

MEDICAL IMPLANTS

CROSS-REFERENCE TO RELATED APPLICATION

This application is a National Stage of International Application No. PCT/US2003/026060, filed Aug. 19, 2003, which claims the benefit of U.S. Provisional Application No. 60/404,509, filed Aug. 19, 2002.

FIELD OF THE INVENTION

The present invention relates to medical implants made of bulk-solidifying amorphous alloys and methods of making such implants.

BACKGROUND OF THE INVENTION

A medical implant is any implant that embeds or attaches as a mechanical device or part in the tissues or organs of the body to achieve or enhance one or more biological functionality. In some cases such mechanical devices or parts may completely replace the function of the relevant body parts, such as tissues or organs, and more specifically, the bones, joints, ligaments, and muscles.

One universal requirement of implants, wherever they are used in the body, is the ability to form a suitably stable mechanical connection with neighboring hard or soft tissues. An unstable implant may function less efficiently, or cease functioning completely, which may induce excessive tissue response. In addition, it has been recognized that all implants should achieve a biological functionality, that is, the implant must meet several requirements for compatibility such as biological, mechanical, and morphological compatibility.

Depending on the primary function of the medical implant, the implant itself can take several forms. For example, in one form implants act as a load-bearing member instead, or in conjunction with, natural load-bearing members of the body such as bone. In such cases, a high strength material with an elastic modulus close to that of the bone which the implant is replacing or attaching to has been sought. In another form implants can be the whole or a part of articulating joints, such as a hip-joint. In such cases, materials with high wear and fretting resistance is desired. In still other forms implants can be cheek-bones, tooth implants, skull plates, fracture plates, intra-medullary rods, bone screws, etc.

Generally, the materials chosen for medical implants have been adapted for the use from materials developed for applications other than medical implants. As a result, such materials have not been always satisfactory. Moreover, the manufacturing of medical implants has also been a major issue as the fabrication of intricate shapes and surface finishing has either limited the desired functionality of such implants or increased the cost of making such implants substantially.

Accordingly, a new class of materials is needed to address the material and manufacturing deficiencies of current materials as well as to provide options and tailorable properties for the various demands of medical implants.

SUMMARY OF THE INVENTION

The current invention is directed to a medical implant made of bulk-solidifying amorphous alloys and methods of making such medical implants, wherein the medical implants are biologically, mechanically, and morphologically compatible with the surrounding implanted region of the body.

In one embodiment of the invention, the medical implant is made of a bulk-solidifying amorphous alloy. In one preferred embodiment of the invention, the medical implant is made of Zr/Ti base bulk-solidifying amorphous alloy with in-situ ductile crystalline precipitates. In another preferred embodiment of the invention, the medical implant has biological, mechanical and morphological compatibility; and is made of Zr/Ti base bulk-solidifying amorphous alloy with in-situ bcc crystalline precipitates of the base-metal. In another preferred embodiment of the invention, the medical implant is made of Zr/Ti base bulk-solidifying amorphous alloy with no Nickel. In still another preferred embodiment of the invention, the medical implant is made of Zr/Ti base bulk-solidifying amorphous alloy with no Aluminum. In yet another preferred embodiment of the invention, the medical implant is made of Zr/Ti base bulk-solidifying amorphous alloy with no Beryllium.

In one preferred embodiment of the invention, a medical implant has biological, mechanical and morphological compatibility; and is made of Zr/Ti based bulk-solidifying amorphous alloy. In another preferred embodiment of the invention, a medical implant has biological, mechanical and morphological compatibility; and is made of Zr-based bulk-solidifying amorphous alloy.

In another embodiment of the invention, the medical implant comprises a portion made at least in part of an implantation material other than bone.

In still another embodiment of the invention, the bulk solidifying amorphous alloy component of the medical implant is coated with a biocompatible polymethyl methacrylate resin cement, which is reinforced with selected oxides including alumina, magnesia, zirconia, or a combination of these oxides along with an application of a small amount of a metal primer agent.

In yet another embodiment of the invention, the medical implant functions as a load-bearing member.

In still yet another embodiment of the invention, the medical implant functions as at least a portion of an articulating joint. In such an embodiment, the medical implant may comprise an articulating bearing surface of the joint.

In still yet another embodiment the invention is directed to a method of forming a medical implant. In one such embodiment, a molten piece of bulk-solidifying amorphous alloy is cast into near-to-net shape component for a medical implant. In another preferred embodiment of the invention, a feedstock of bulk-solidifying amorphous alloy is heated to around the glass transition temperature and formed into a near-to-net shape component for a medical implant.

In still yet another embodiment of the invention, the surface of the medical implant is modified by chemical treatment. In such an embodiment, the chemical treatment may use a mixed aqueous solution of hydrofluoric acid or nitric acid or sodium hydroxide, or a thermal treatment under in-air oxidation, or a combination of aforementioned treatments.

In still yet another embodiment of the invention, the surface topography of the medical implant has pores with a diameter between about 10 to 500 $\mu$m, preferably between about 100 to 500 $\mu$m, and most preferably between about 100 to 200 $\mu$m.

In still yet another embodiment of the invention, the surface topography of the medical implant has an average roughness of between 1 to 50 $\mu$m.

In still yet another embodiment of the invention, the surface topography of the medical implant has a concave texture, convex texture or both.

In still yet another embodiment, the invention is directed to a method of fabricating a medical implant of a bulk-solidifying amorphous alloys.

In still yet another embodiment, the invention is directed to a method of duplicating desired morphological features onto the surface of the medical implant.

BRIEF DESCRIPTION OF THE DRAWINGS

These and other features and advantages of the present invention will be better understood by reference to the following detailed description when considered in conjunction with the accompanying drawing wherein.

DETAILED DESCRIPTION OF THE INVENTION

Figure 1:
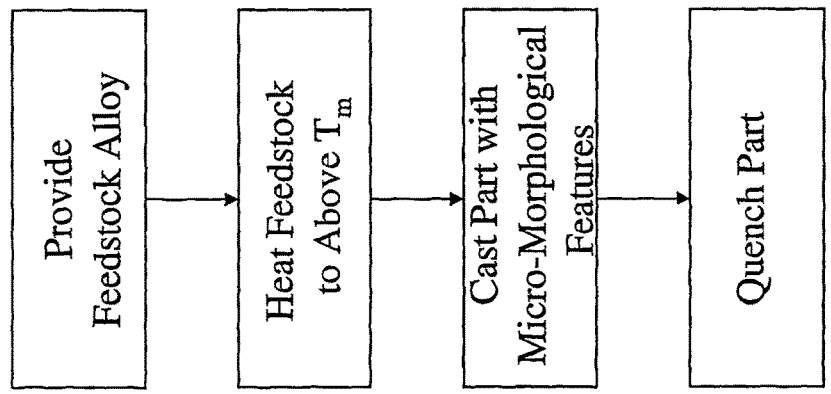
FIG. 1 shows a flow-chart an exemplary embodiment of a method of reproducing surface morphological features on a medical implant according to the current invention.

The current invention is directed to medical implants made of bulk-solidifying amorphous alloys capable of providing biological, mechanical, and morphological compatibility, and methods of making such medical implants.

Bulk solidifying amorphous alloys are a recently discovered family of amorphous alloys, which can be cooled at substantially lower cooling rates, of about 500 K/sec or less, and substantially retain their amorphous atomic structure. As such, these materials can be produced in thickness of 1.0 mm or more, substantially thicker than conventional amorphous alloys of typically 0.020 mm which require cooling rates of $10^5$ K/sec or more. Exemplary alloy materials are described in U.S. Pat. Nos. 5,288,344; 5,368,659; 5,618,359; and 5,735,975 (the disclosures of which are incorporated in their entirety herein by reference).

One exemplary family of bulk solidifying amorphous alloys can be described as $(Zr,Ti)_a(Ni,Cu,Fe)_b(Be,Al,Si,B)_c$, where a is in the range of from 30 to 75, b is in the range of from 5 to 60, and c in the range of from 0 to 50 in atomic percentages. Furthermore, those alloys can accommodate substantial amounts of other transition metals up to 20% atomic, and more preferably metals such as Nb, Cr, V, Co. A preferable alloy family is $(Zr,Ti)_a(Ni,Cu)_b(Be)_c$, where a is in the range of from 40 to 75, b is in the range of from 5 to 50, and c in the range of from 5 to 50 in atomic percentages. Still, a more preferable composition is $(Zr,Ti)_a(Ni,Cu)_b(Be)_c$, where a is in the range of from 45 to 65, b is in the range of from 7.5 to 35, and c in the range of from 10 to 37.5 in atomic percentages. Another preferable alloy family is $(Zr)_a(Nb,Ti)_b(Ni,Cu)_c(Al)_d$, where a is in the range of from 45 to 65, b is in the range of from 0 to 10, c is in the range of from 20 to 40 and d in the range of from 7.5 to 15 in atomic percentages. These bulk-solidifying amorphous alloys can sustain strains up to 1.5% or more and generally around 1.8% without any permanent deformation or breakage. Further, they have high fracture toughness of 10 ksi-sqrt(in) (sqrt: square root) or more, and preferably 20 ksi sqrt(in) or more. Also, they have high hardness values of 4 GPa or more, and preferably 5.5 GPa or more. The yield strength of bulk solidifying alloys range from 1.6 GPa and reach up to 2 GPa and more exceeding the current state of the Titanium alloys. Further, Zr-base bulk-solidifying amorphous alloys have a generally lower modulus of elasticity than Ti-base bulk-solidifying amorphous alloys, and have more robust processability characteristics, which allows a better casting of the desired micro-structured surface features.

Another set of bulk-solidifying amorphous alloys are ferrous metals (Fe, Ni, Co) based compositions. Examples of such compositions are disclosed in U.S. Pat. No. 6,325,868; (A. Inoue et. al., Appl. Phys. Lett., Volume 71, p 464 (1997)); (Shen et. al., Mater. Trans., JIM, Volume 42, p 2136 (2001)); and Japanese patent application 2000126277 (Publ. #.2001303218 A), all of which are incorporated herein by reference. One exemplary composition of such alloys is $Fe_{72}Al_5Ga_2P_{11}C_6B_4$. Another exemplary composition of such alloys is $Fe_{72}Al_7Zr_{10}Mo_5W_2B_{15}$. Although, these alloy compositions are not processable to the degree of the above-cited Zr-base alloy systems, they can still be processed in thicknesses around 1.0 mm or more, sufficient enough to be utilized in the current invention. Similarly, these materials have elastic strain limits higher than 1.2% and generally around 1.8%. The yield strength of these ferrous-based bulk-solidifying amorphous alloys is also higher than the Zr-based alloys, ranging from 2.5 GPa to 4 GPa, or more. Ferrous metal-base bulk amorphous alloys also very high yield hardness ranging from 7.5 GPA to 12 GPa.

In general, crystalline precipitates in bulk amorphous alloys are highly detrimental to the properties of bulk-solidifying amorphous alloys, especially to the toughness and strength of these materials, and, as such, such precipitates are generally kept to as small a volume fraction as possible. However, there are cases in which, ductile crystalline phases precipitate in-situ during the processing of bulk amorphous alloys, are indeed beneficial to the properties of bulk amorphous alloys, and especially to the toughness and ductility of the materials. Such bulk amorphous alloys comprising such beneficial precipitates are also included in the current invention. An exemplary composition of such alloy is $Zr_{56.2}Ti_{13.8}Nb_{5.0}Cu_{6.9}Ni_{5.6}Be_{12.5}$ in atomic percentages. This alloy has a low elastic modulus of from 70 GPa to 80 GPa depending on the specific microstructure of ductile-crystalline precipitates. Further, the elastic strain limit is 1.8% or more and the yield strength is 1.4 GPa and more.

Although a number of bulk solidifying amorphous alloy compositions are described above, the alloy can also be preferably selected to be free of Ni or Al or Be in order to address high sensitivity or allergy of specific population groups to such metals.

Applicants have discovered that bulk-solidifying amorphous alloys have general characteristics, which are particularly useful in medical implants. These characteristics, as will be shown below, make bulk-solidifying amorphous alloys uniquely suited as a class of materials for use in medical implants.

First, bulk-solidifying amorphous alloys have an elastic modulus that is typically 15 to 25% lower than the conventional alloys of its constituent elements. This decreased elastic modulus is the direct result of the amorphous atomic structure of the alloys, which lacks long-range atomic order as in the case of conventional crystalline metals. For example, a titanium base crystalline alloy (such as Ti-6-4, which is commonly used in medical implants) has an elastic modulus typically around 120 GPa, whereas Ti-base amorphous alloys have an elastic modulus around or below 100 GPa. This decreased elastic modulus is particularly desirable because bone has an elastic modulus of about 20 GPa or less, and implant materials with an elastic modulus closer to the elastic modulus of bone have better biological functionality, especially when the implant is used as a load-bearing member. Specifically, the better the match between the elastic modulus of the implant material and the elastic modulus of the replacement bone, the better the implant will integrate with the surrounding or associated bone, and function in a more coherent manner, thereby allowing the surrounding or associated bones to absorb a fair share of the stress loading. However, where materials with relatively high elastic modulus are used, the surrounding or associated bones will take less of the loading, and as a result will not be able to function in their normal manner, and ultimately may cause bone-thinning or failure of the implant.

Secondly, bulk-solidifying amorphous alloys typically have yield strengths of at least 50% higher than conventional alloys of made of similar constituent elements. For example, a titanium base crystalline alloy (such as Ti-6-4, which is commonly used in medical implants) has a yield strength typically around 850 MPa, whereas Ti-base amorphous alloys have a yield strength around 1900 MPa. The combination of such low modulus and high yield strength makes it possible to manufacture a durable and strong load-bearing medical implant with high mechanical functionality.

Further, bulk solidifying amorphous alloys have a very high elastic strain limit, which characterizes a material's ability to sustain strains without permanent deformation. Typically bulk-solidifying amorphous alloys have elastic strain limits of around 1.8% or higher. The elastic strain limit is another important characteristic of materials for use in medical implants, and one that is of particular importance for implant members subject to any mechanical loading. However, conventional implant materials generally have very poor elastic strain limit properties. For example, conventional metals and alloys used as implant materials have elastic strain limit below 0.9%, which indicates that these materials are not able to sustain very large global and local loading without some minimal or even permanent deformation of the implant material. A high elastic strain limit also helps to maintain the surface morphology of the implant and, as such, precludes excessive tissue response. In the case of conventional metals and alloys with very low elastic strain limits, the use of larger and much more rigid implants is generally needed to sustain both loading on global and local loading as well as to maintain the integrity of the implant's surface morphology. However, larger implants and rigid implant structures are highly undesirable because of the increased operational and surgical complications from implementing larger implant structures as well as "bone thinning" in the associated bones.

Another important requirement for an implant material is to have a suitable surface morphology. For example, in a scientific article published by Oshida ("Fractal Dimension Analysis Of Mandibular Bones: Toward A Morphological Compatibility Of Implants" in Bio-Medical Materials and Engineering, 1994, 4:397407), the disclosure of which is incorporated herein by reference, it was found that surface morphology of successful implants has upper and lower limitations in average roughness (1~50 μm) and average particle size (10~500 μm), regardless of the type of implant material (metallic, ceramics, or polymeric materials) used. For example, it has been shown that if an implant material has a particle size smaller than 10 μm, the surface of the implant will be more toxic to fibroblastic cells and have an adverse influence on cells due to their physical presence independent of any chemical toxic effects. Likewise, if the pore size of the implant material is larger than 500 μm, the surface does not exhibit sufficient structural integrity because it is too coarse. Therefore, morphological compatibility is an important factor in implant design, and is now well accepted in the field of implants.

Unfortunately due to the small dimensions of acceptable morphological features, desired surface morphology cannot be readily produced onto current implant materials. Instead, mechanical and chemical methods, such as shot peening and acid etching, are used to fabricate surface morphology onto the implant material after the shaping and fabrication of the actual implant body. Because of the statistical nature of these conventional techniques only surface morphologies with relatively crude and random features and lacking consistency and precision both in the shape and the distribution of desired surface features have been produced. Indeed, the production of suitable surface morphologies can be said to be the result of statistical accidents rather than by design.

Applicants have found that it is possible to form microstructured surface morphologies by design using bulk-solidifying amorphous alloys. The unique amorphous atomic microstructure of these materials responds uniformly to the forming operations of micron and sub-micron scale making it possible to form features within the desirable morphological ranges. This is in distinct contrast to conventional metals and alloys, where the microstructure of the material is characterized by crystallites (individual grains typically with dimensions of few to several hundreds microns) each of which has different crystallographic orientation and, as such, responds non-uniformly to shaping and forming operations.

The micro-structured surface morphology according to the current invention can be produced in two alternative ways. In a first exemplary method, as outlined in FIG. 1, the surface morphology can be simultaneously formed during the fabrication of implant components by casting methods. In such an embodiment the mold surfaces used in the casting operation can be pre-configured to have the negative impression of the desired surface microstructure so that the bulk-solidifying amorphous alloy replicates such features upon casting. The relatively low melting temperature of bulk-solidifying amorphous alloys and the lack of any first-order phase transformation during the solidification readily enables the replication of micron sized mold features during the casting of the implant components. The solidification shrinkage is then dominated by the coefficient of thermal expansion rather than the volume difference between the solid and liquid state of the casting alloy. Accordingly, bulk amorphous alloys with low coefficients of thermal expansion (at temperatures from ambient to glass transition) are preferred. For example, Zr-base bulk solidifying amorphous alloys generally have a coefficient of thermal expansion of around $10^{-5}$ (m/m ° C.) providing low shrinkage rates. Such a process is highly desirable as several steps of post-finishing and surface preparation operations can be reduced or eliminated.

Figure 2:
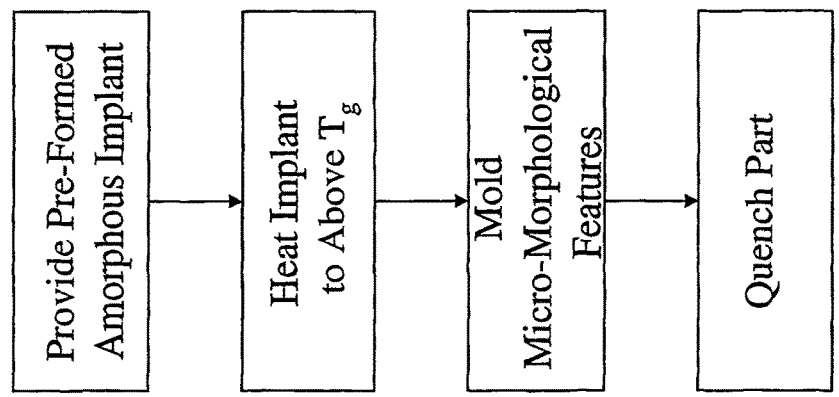
FIG. 2 shows a flow-chart another exemplary embodiment of a method of reproducing surface morphological features on a medical implant according to the current invention.

In an alternative exemplary method, as outlined in FIG. 2, a pre-fabricated implant component made of bulk-solidifying amorphous alloy is subjected to a surface micro-structuring process at around the glass transition temperature of the bulk-solidifying amorphous alloy material. In such an embodiment, the fabricated implant component is heated to around the glass transition temperature and pressed against a mold having the negative impression of the desired surface microstructure. Alternatively, a mold heated around about the glass transition temperature of the amorphous alloy can be brought into contact with the fabricated implant component to make a surface impression and form the microstructured surface features. As the bulk solidifying amorphous alloy will readily transition into a viscous liquid regime upon heating, the replication of the desired surface morphology can readily take place. In this embodiment of the method, bulk-solidifying amorphous alloys with a large ΔTsc (supercooled liquid region) are preferred. For example, bulk-solidifying amorphous alloys with a ΔTsc of more than 60° C., and still more preferably a ΔTsc of 90° C. and more are desired for their ability to reproduce high-definition surface micro-structuring. One exemplary embodiment of an alloy having a ΔTsc of more than 90° C. is $Zr_{47}Ti_8Ni_{10}Cu_{7.5}Be_{27.5}$. ΔTsc is defined as the difference between Tx (the onset temperature of crystallization) and Tsc (the onset temperature of super-cooled liquid region). These values can be conveniently determined by using standard calorimetric techniques such as by DSC measurements at 20° C./min.

Regardless of the method utilized, the surface microstructure can take several forms depending on the specific application. For example, in one embodiment, the surface microstructure can have relatively minute features (such as with typical dimensions of around 10 microns). In another embodiment, the surface feature can have gross features (such as with typical dimensions of around 100 microns or more). In this latter case, the surface can be subjected to other surface treatments, such as chemical treatment to further improve the surface morphology. It should further be understood that, the bulk-solidifying amorphous alloys may be processed to produce consistent and precise surface microstructures of both currently known and used morphologies, and also novel surface morphologies unavailable in current medical implant materials.

The composition of bulk-solidifying amorphous alloys can be selected to address specific needs for various implants. For example, Zr/Ti base bulk-solidifying amorphous alloys are preferred for improved corrosion resistance and bio-compatibility. Zr-base bulk-solidifying amorphous alloys are especially preferred for still lower elastic modulus.

Figure 3:
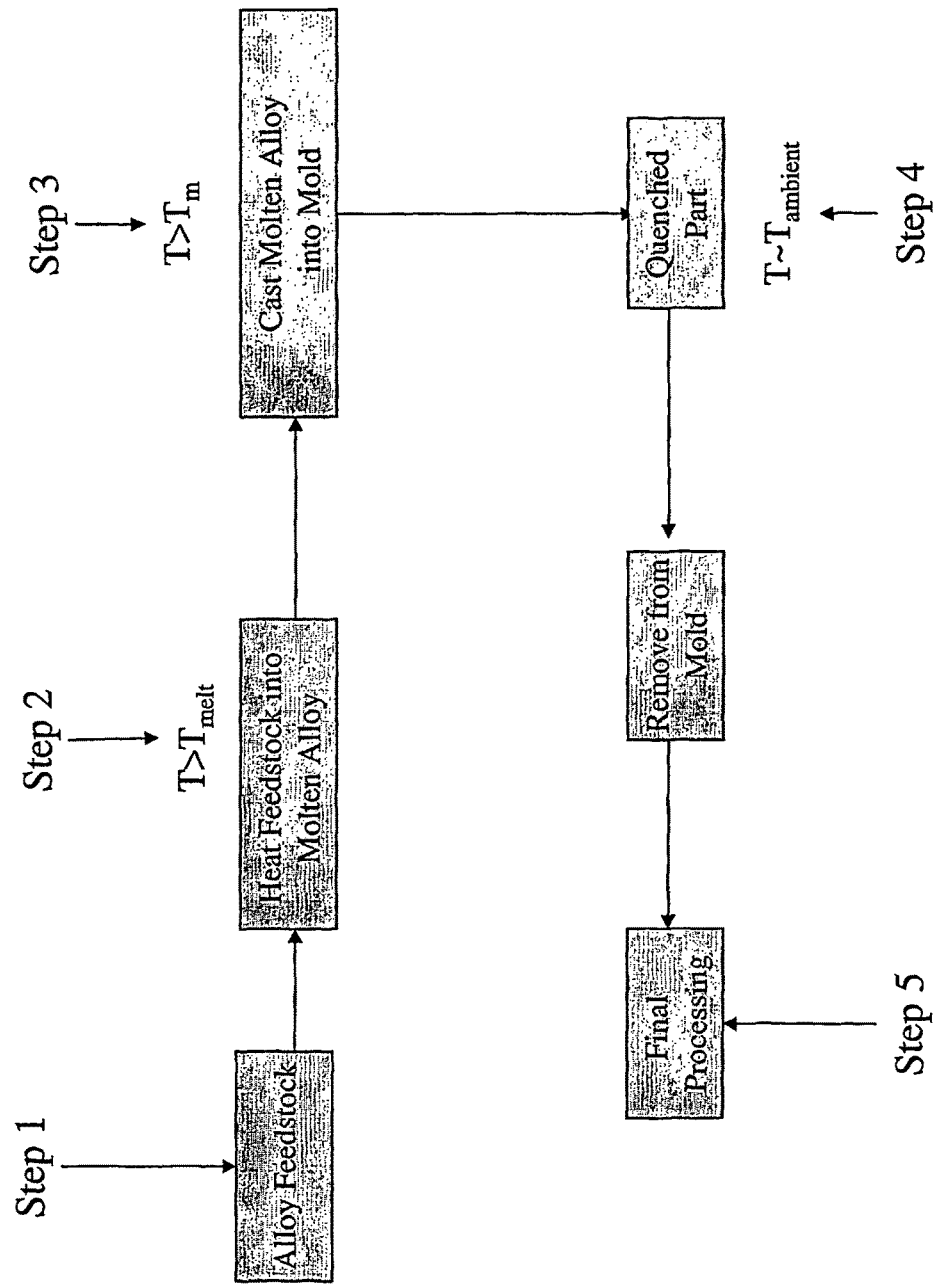
FIG. 3 shows a flow-chart an exemplary embodiment of a method of producing a medical implant according to the current invention.

This invention is also directed to methods of fabricating medical implants of bulk-solidifying amorphous alloys. In a first exemplary embodiment, as outlined in FIG. 3, the medical implants may be fabricated by a casting process as described in the following. A feedstock of bulk-solidifying amorphous alloy (Step 1) is provided, which does not necessarily have any amorphous phase. The feedstock is then heated above the melting temperature (Step 2) of the bulk-solidifying amorphous alloy and the molten alloy is then introduced into a suitable mold (Step 3) having the shape of the desired medical implant. The molten alloy can be introduced into the mold by various means such as by injection of gas or piston pressure, by vacuum suction, and vacuum assisted counter gravity casting. The molten alloy is then quenched (Step 4) at cooling rates sufficient to form a substantially amorphous phase having an elastic strain limit of 1.5% or higher. The mold surface can have the negative impressions of the desired morphology as described above. This process allows the production of high-strength medical implant components with near-net-shape tolerances to the actual component, and, as such, substantial cost savings can be achieved by reducing the post-casting process (Step 5) and achieving closer tolerances to the actual component. The provided bulk solidifying amorphous alloy is such that, it has a critical cooling rate of less than 1,000° C./sec, so that section thicknesses greater than 0.5 mm can be readily cast into an amorphous structure during the fabrication of a dental prosthesis. However, more preferably, the critical cooling rate is less than 100° C./sec and most preferably less than 10° C./sec. In one preferred embodiment of the invention, the dental prosthesis is cast by providing a bulk-solidifying amorphous alloy having a coefficient of thermal expansion of less than about $10^{-5}$ (m/m ° C.), and a glass transition temperature of less than 400° C., and preferably less than 300° C., in order to achieve a high level of replication of prosthesis mold features after casting.

Figure 4:
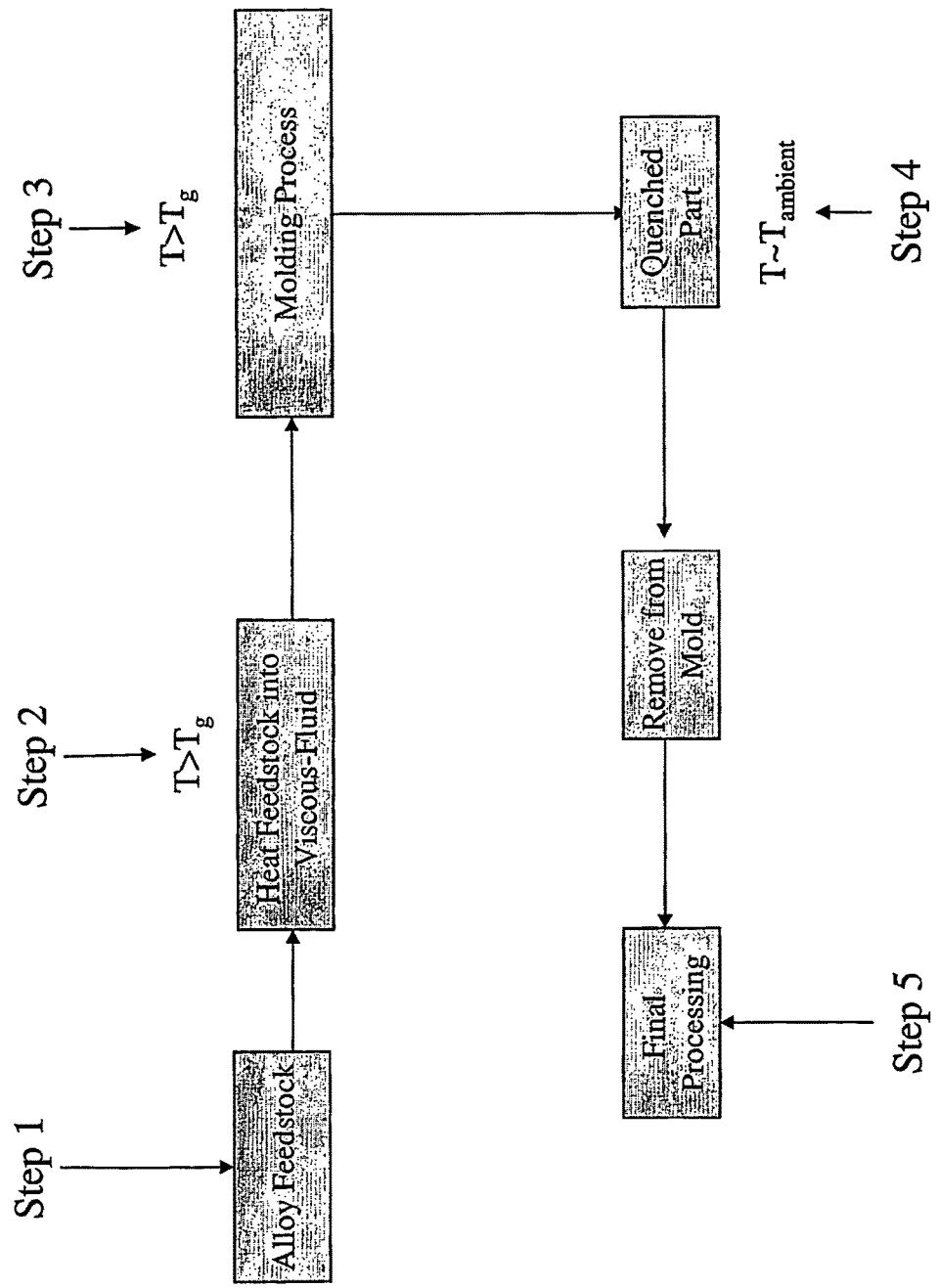
FIG. 4 shows a flow-chart another exemplary embodiment of a method of producing a medical implant according to the current invention.

In an alternative method, as outlined in FIG. 4, a substantially amorphous feedstock of a bulk-solidifying amorphous alloy is provided (Step 1). The feedstock is then heated around the glass temperature of the bulk-solidifying amorphous alloy to reach the viscous-fluid regime (Step 2). The viscous alloy is then forced against or onto a suitable mold (Step 3) having the shape of the desired medical implant. When the desired implant shape is formed, the viscous alloy is then quenched (Step 4) to retain the substantially amorphous phase having an elastic strain limit of 1.5% or higher. The mold surface can have the negative impressions of the desired morphology as described above. Again, this process also allows producing high-strength medical implant components with near-net-shape tolerances to the actual component, and, as such, substantial cost savings can be achieved by reducing the post-casting process (Step 5) and achieving closer tolerances to the actual component. In this embodiment of the method, bulk-solidifying amorphous alloys with a large ΔTsc (supercooled liquid region) are preferred. Again, for example, bulk-solidifying amorphous alloys with a ΔTsc of more than 60° C., and still more preferably a ΔTsc of 90° C. and more are desired because they possess the desired mechanical properties, such as high-elastic strain limit, and because of the ease of fabricating these materials.

Furthermore, permanent molds, such as metallic dies, can be employed in the above mentioned processes of fabricating implant components and surface micro-structuring processes. Such use of permanent molds in the fabrication of high strength implant components is unique to bulk-solidifying amorphous alloys. Generally, such permanent mold processes with high-strength conventional materials are not suitable for the fabrication of implant components, as various issues such as severe reaction with mold, casting defects, micro-structural uniformity, and proper mold fill can not be satisfactorily addressed. Accordingly, the use of permanent mold provides distinct advantages to bulk-solidifying amorphous in the use and method of fabrication for medical implants, as higher through-put, better consistency, both in general dimensions and surface morphology, and lower fabrication costs can be achieved.

Although specific embodiments are disclosed herein, it is expected that persons skilled in the art can and will design medical implants and methods of making such devices that are within the scope of the following description either literally or under the Doctrine of Equivalents.

What is claimed is:

1. An implant for placement into an implant region comprising:
    an implant body at least partially constructed of a bulk-solidifying amorphous alloy that is free from Ni and Al and having an elastic strain limit of around 1.2% or more, wherein the implant body has a plurality of surface features formed of the bulk-solidifying amorphous alloy having a feature size ranging from about 10 to 500 μm on an outer surface thereof, wherein the bulk-solidifying amorphous alloy comprises a ductile metallic crystalline phase precipitate and the implant body surface has an average roughness of between 1 to 50 μm.

2. The implant as described in claim 1, wherein the plurality of surface features on the outer surface of the implant body comprise a plurality of pores with diameters between about 10 to 500 μm.

3. The implant as described in claim 1, wherein the plurality of surface features on the outer surface of the implant body comprise a plurality of pores with diameters between about 100 to 500 μm.

4. The implant as described in claim 1, wherein the plurality of surface features on the outer surface of the implant body comprise a plurality of pores with diameters between about 100 to 200 μm.

5. The implant as described in claim 1, wherein the plurality of surface features on the outer surface of the implant body comprise a surface texture selected from the group consisting of concave, convex, and mixture of concave and convex.

6. The implant as described in claim 1, wherein the bulk-solidifying amorphous alloy has an elastic strain limit of around 1.8% or more.

7. The implant as described in claim 1, wherein the bulk-solidifying amorphous alloy has a high fracture toughness of at least about 10 ksi-in.

8. The implant as described in claim 1, wherein the bulk-solidifying amorphous alloy has a high hardness value of at least about 5.0 GPa.

9. The implant as described in claim 1, wherein the bulk-solidifying amorphous alloy comprises Fe.

10. The implant of claim 9, wherein the bulk-solidifying amorphous alloy comprises Zr and Ti.

11. The implant as described in claim 1, wherein at least a portion of the implant body is constructed of a conventional implantation material.

12. The implant as described in claim 1, wherein at least a portion of the implant body is coated with a biocompatible resin cement.

13. The implant as described in claim 1, wherein the portion of the implant body formed from the bulk-solidifying amorphous alloy has a section thickness of at least 0.5 mm.

14. The implant as described in claim 1, wherein the implant body is in the form of a load bearing member.

15. The implant as described in claim 1, wherein the implant body is in the form of an articulating joint.

16. The implant as described in claim 1, wherein the bulk-solidifying amorphous alloy has a supercooled liquid region of more than 90 □C.

17. The implant of claim 1, wherein the outer surface of the implant body has biological, mechanical and morphological compatibility with the implant region.

18. The implant of claim 1, wherein the bulk-solidifying amorphous alloy having a composition that is free from Be.

19. The implant of claim 1, wherein the bulk-solidifying amorphous alloy further comprises Co.

20. The implant of claim 1, wherein the bulk-solidifying amorphous alloy further comprises Be.

21. The implant of claim 1, wherein the bulk-solidifying amorphous alloy has a glass transition temperature of 500° C. or above.

22. An implant comprising a bulk-solidifying amorphous alloy that is free from Ni and Al and having an elastic strain limit of about 1.2% or more, a high hardness value of at least about 4 GPa, a glass transition temperature of 500° C. or above, and a coefficient of thermal expansion of about 10-5 (m/m ° C.) or less, wherein the bulk-solidifying amorphous alloy comprises a ductile metallic crystalline phase precipitate and the implant includes a body surface having an average roughness of between 1 to 50 μm.

23. The implant of claim 22, wherein the bulk-solidifying amorphous alloy has the glass transition temperature of 550° C. or above.

24. The implant of claim 22, wherein the bulk-solidifying amorphous alloy comprises Fe.

* * * * *